US012766332B2

(12) United States Patent
Ho

(10) Patent No.: US 12,766,332 B2
(45) Date of Patent: Oct. 20, 2026

(54) MAGNETIC STIMULATION WITH RANDOM VARIABLE PULSED INTERVALS

(71) Applicant: VENITAS RESEARCH CENTER, INC., Keelung City (TW)

(72) Inventor: Conway Ho, La Palma, CA (US)

(73) Assignee: Venitas Research Center, Inc., Keelung City (TW)

( * ) Notice: Subject to any disclaimer, the term of this patent is extended or adjusted under 35 U.S.C. 154(b) by 1171 days.

(21) Appl. No.: 17/555,486

(22) Filed: Dec. 19, 2021

(65) Prior Publication Data

US 2022/0111222 A1 Apr. 14, 2022

Related U.S. Application Data

(63) Continuation-in-part of application No. 16/365,676, filed on Mar. 27, 2019, now Pat. No. 11,406,841.

(51) Int. Cl.
*A61N 2/00* (2006.01)

(52) U.S. Cl.
CPC .................................... *A61N 2/006* (2013.01)

(58) Field of Classification Search
CPC ...... A61N 2/006; A61N 2/02; A61B 5/04004; A61B 5/0476; A61B 5/4836; A61B 5/165; A61B 5/726; A61B 5/0482
See application file for complete search history.

(56) References Cited

U.S. PATENT DOCUMENTS

| | | | | |
|---|---|---|---|---|
| 6,488,617 | B1 | 12/2002 | Katz | |
| 9,308,385 | B2 | 4/2016 | Jin | |
| 2009/0082690 | A1 | 3/2009 | Phillips et al. | |
| 2016/0175589 | A1* | 6/2016 | Wingeier ............ | A61B 5/4836 607/45 |
| 2019/0082990 | A1* | 3/2019 | Poltorak ............. | A61B 5/7267 |

* cited by examiner

*Primary Examiner* — Carrie R Dorna
*Assistant Examiner* — Joshua Daryl D Lannu
(74) *Attorney, Agent, or Firm* — SALIWANCHIK, LLOYD & EISENSCHENK

(57) ABSTRACT

A method of modulating a brain activity of a mammal is achieved by subjecting the mammal to transcranial magnetic stimulation (TMS) with a TMS apparatus at random variable pulse intervals for a time sufficient to modulate said brain activity. The method can also be used by administering electric stimulation to the brain. Improvement in a physiological condition or a clinical condition is achieved. Conditions to be treated include but are not limited to PTSD, autism spectrum disorder addiction (SUD) and Alzheimer's disease.

2 Claims, 11 Drawing Sheets

| 3.02-4.36 Hz AmpSum | 4.88-7.16 Hz AmpSum | 7.81-9.68 Hz AmpSum |
|---|---|---|
| 0.598 | 0.607 | 0.772 |
| 0.525 | 0.577 | 0.840 |
| 0.570 | 0.435 | 0.691 |
| 0.725 | 0.661 | 1.103 |
| 0.841 | 0.735 | 1.247 |
| 0.740 | 0.719 | 1.114 |
| 0.467 | 0.532 | 0.650 |
| 0.490 | 0.505 | 0.567 |
| 0.771 | 0.814 | 0.993 |
| 1.084 | 0.981 | 1.281 |
| 0.807 | 0.824 | 1.080 |
| 0.381 | 0.428 | 0.476 |
| 0.527 | 0.554 | 0.591 |
| 0.792 | 0.682 | 0.908 |
| 0.951 | 0.692 | 0.991 |
| 0.867 | 0.621 | 0.958 |
| 0.664 | 0.614 | 0.654 |
| 0.813 | 0.777 | 0.720 |
| 0.914 | 0.666 | 0.684 |

3.02-4.36 Hz AmpSum 4.88-7.16 Hz AmpSum 7.81-9.68 Hz AmpSum

| 1.91-4.56 Hz AmpSum | 4.82-6.99 Hz AmpSum | 7.42-10.12 Hz AmpSum |
|---|---|---|
| 2.856 | 2.306 | 11.815 |
| 2.554 | 2.329 | 11.643 |
| 2.210 | 1.424 | 7.778 |
| 2.912 | 2.951 | 16.929 |
| 3.493 | 3.626 | 19.812 |
| 2.918 | 2.930 | 15.699 |
| 1.744 | 1.651 | 6.030 |
| 1.382 | 1.425 | 11.341 |
| 2.468 | 2.771 | 14.884 |
| 4.060 | 4.200 | 11.017 |
| 2.238 | 2.410 | 7.107 |
| 1.133 | 1.086 | 3.028 |
| 3.682 | 3.253 | 30.780 |
| 3.090 | 3.521 | 29.459 |
| 4.042 | 4.161 | 21.440 |
| 3.136 | 2.649 | 15.151 |
| 5.559 | 2.614 | 15.529 |
| 3.915 | 3.027 | 24.126 |
| 6.542 | 3.861 | 26.823 |

1.91-4.56 Hz AmpSum 4.82-6.99 Hz AmpSum 7.42-10.12 Hz AmpSum

| 7.10-9.91 Hz AmpSum | 10.12-12.82 Hz AmpSum | 13.48-21.03 Hz AmpSum |
|---|---|---|
| 7.978 | 6.626 | 9.419 |
| 7.644 | 6.366 | 9.258 |
| 7.917 | 5.389 | 6.720 |
| 11.665 | 11.029 | 11.823 |
| 14.196 | 12.061 | 13.537 |
| 10.595 | 9.841 | 11.474 |
| 8.766 | 4.291 | 6.290 |
| 9.912 | 7.034 | 4.785 |
| 12.409 | 13.063 | 11.028 |
| 16.379 | 14.865 | 12.938 |
| 11.668 | 12.197 | 9.330 |
| 8.890 | 4.369 | 3.908 |
| 10.201 | 13.712 | 6.160 |
| 13.447 | 19.944 | 10.917 |
| 15.187 | 22.104 | 10.331 |
| 12.618 | 16.381 | 7.907 |
| 9.427 | 10.895 | 4.534 |
| 12.310 | 25.014 | 7.126 |
| 11.749 | 21.120 | 5.679 |

7.10-9.91 Hz AmpSum 10.12-12.82 Hz AmpSum 13.48-21.03 Hz AmpSum

| 10.86-12.40 Hz AmpSum | 12.50-15.20 Hz AmpSum | 16.00-23.57 Hz AmpSum |
|---|---|---|
| 7.639 | 5.748 | 4.377 |
| 8.476 | 7.296 | 4.737 |
| 6.304 | 4.477 | 3.361 |
| 9.911 | 11.622 | 5.083 |
| 9.419 | 16.002 | 5.678 |
| 9.339 | 13.975 | 5.711 |
| 6.137 | 5.754 | 3.774 |
| 3.661 | 4.563 | 1.881 |
| 7.799 | 18.019 | 3.929 |
| 7.864 | 28.729 | 5.259 |
| 7.235 | 21.048 | 4.260 |
| 3.422 | 5.512 | 1.969 |
| 4.609 | 9.522 | 1.776 |
| 7.500 | 28.561 | 3.188 |
| 7.373 | 37.653 | 3.498 |
| 6.597 | 26.255 | 2.998 |
| 4.010 | 10.991 | 1.924 |
| 5.473 | 18.806 | 2.060 |
| 4.550 | 16.272 | 1.923 |

| 7.31-8.48 Hz AmpSum | 8.85-9.75 Hz AmpSum | 10.35-11.49 Hz AmpSum |
|---|---|---|
| 2.588 | 3.381 | 2.388 |
| 2.845 | 3.501 | 2.556 |
| 2.063 | 2.097 | 1.541 |
| 4.653 | 5.478 | 5.665 |
| 5.842 | 6.604 | 6.676 |
| 4.746 | 5.670 | 5.954 |
| 2.944 | 2.897 | 2.225 |
| 1.994 | 1.573 | 1.989 |
| 5.645 | 5.116 | 7.193 |
| 8.492 | 8.398 | 11.292 |
| 5.813 | 6.444 | 9.478 |
| 2.878 | 2.490 | 2.450 |
| 4.011 | 4.527 | 5.423 |
| 7.103 | 6.793 | 11.737 |
| 8.859 | 9.196 | 15.566 |
| 7.323 | 8.744 | 15.140 |
| 4.769 | 5.284 | 7.570 |
| 6.768 | 9.589 | 9.390 |
| 7.155 | 9.784 | 12.637 |

| 6.78-7.95 Hz AmpSum | 8.42-9.32 Hz AmpSum | 10.12-11.28 Hz AmpSum |
|---|---|---|
| 0.709 | 1.688 | 0.588 |
| 0.671 | 1.806 | 0.605 |
| 0.472 | 1.071 | 0.516 |
| 0.782 | 2.027 | 0.785 |
| 0.799 | 2.269 | 0.765 |
| 0.708 | 2.221 | 0.716 |
| 0.521 | 1.690 | 0.534 |
| 0.429 | 0.950 | 0.633 |
| 0.720 | 1.997 | 0.885 |
| 0.730 | 2.515 | 0.910 |
| 0.628 | 2.493 | 0.894 |
| 0.404 | 1.605 | 0.631 |
| 0.630 | 1.552 | 1.302 |
| 0.733 | 2.074 | 1.290 |
| 0.734 | 2.553 | 1.395 |
| 0.671 | 2.637 | 1.446 |
| 0.638 | 2.249 | 1.450 |
| 0.724 | 1.969 | 1.814 |
| 0.777 | 2.144 | 1.838 |

MAGNETIC STIMULATION WITH RANDOM VARIABLE PULSED INTERVALS

The present application is a Continuation-in-Part of U.S. application Ser. No. 16/365,676 filed on 27 Mar. 2019 and claims priority to it under 35 U.S.C 120 and additionally claims priority under 35 U.S.C. 119(e) to U.S. Provisional Application No. 62/654,476, filed on Apr. 8, 2018. The disclosure of both of those applications is incorporated herein by reference in their entirety.

FIELD OF THE INVENTION

The present invention relates to methods of modulating brain activity with transcranial magnetic stimulation (TMS) wherein the TMS is administered with variable pulse intervals for a time sufficient to modulate said brain activity wherein an improvement in a physiological condition or a clinical condition is achieved. Preferably, the variable pulse intervals are delivered in a random fashion. The random variable pulse interval settings are derived from a patient's EEG signal that has been extracted from analysis with a filtering process to attenuate EEG frequencies higher and lower than the desired EEG frequencies being targeted including but not limited to wavelet transform analysis, where sets of wavelets are generally needed to analyse data fully. Additionally, the present invention relates to electric stimulation of the brain by administering variable electric pulse intervals for a time sufficient to modulate said brain activity wherein an improvement in a physiological condition or a clinical condition is achieved. Preferably, the variable electric pulse intervals are delivered in a random fashion.

The random variable pulse intervals are preferably delivered in a random fashion with idealized probability distribution.

BACKGROUND OF THE INVENTION

Transcranial magnetic stimulation and rTMS have been used to treat many psychological and medical disorders such as major depressive disorder, Parkinson's disease, PTSD, Alzheimer's disease, autism spectrum disorder (ASD), schizophrenia, pain management and others. Recently, Jin and Phillips, in US Patent Publication 2009/0082690, have disclosed a treatment protocol using rTMS where the output of the magnetic field is adjusted based on a patient's EEG intrinsic frequencies in an attempt to alter the patient's intrinsic EEG frequencies. U.S. Pat. No. 9,308,385 uses a different approach to administer rTMS by using a frequency based on a biological metric or an harmonic of a biological metric.

U.S. Pat. No. 9,308,385 discloses rTMS treatments where the targeted intrinsic identified is treated with an rTMS frequency that is a harmonic or sub-harmonic of a biological metric such as the patient's heart rate.

US2016/0220836A1 discloses a TMS treatment that focuses on an EEG phase calculation and prediction in a given frequency and real time TMS stimuli triggered by the phase locked TTL pulses. The protocol of US2016/0220836A1 uses high frequency bursts (50 Hz) and low frequency bursts (1 Hz) using TMS.

U.S. Pat. No. 9,095,266 to Fu discloses signal processing methods using decomposition and compression techniques to denoise and MEG data that are severely corrupted with noise. The result is a cleaner signal that is used to diagnose a patient by comparison with a neural network. This allows the healthcare practitioner to provide a standard treatment based on the diagnosis. A wavelet analysis is one method disclosed by Fu to assist in denoising signals in order to make a diagnosis. However, the wavelet analysis has no part in determining the treatment therapy.

Su et al *Sci Rep.* 2018; 8: 14456 reports a difference in the effects on motor symptoms of low-frequency stimulation (<100 Hz) and high frequency stimulation (>100 Hz) in Parkinson's patient receiving subthalamic deep brain electric stimulation. HFS was found to be a more effective strategy to alleviate tremors within the medication-off condition and LFS was found to be more helpful for severe akinesia and gait disturbances in patients with PD.

TMS is delivered by an apparatus that is comprised of magnetic coils that provide pulsed magnetic fields. The frequencies and intensity can be varied if desired. Prior to the present invention TMS treatments have consisted of the delivery of a single frequency at a set intensity. The present invention provides a novel TMS delivery system that delivers TMS with random variable pulse intervals. The random variable pulse intervals can follow a pattern or can be random weighted by idealized Gaussian distribution function.

SUMMARY OF THE INVENTION

Briefly, in accordance with the present invention, the brain activity of a mammal is modulated by subjecting the mammal to transcranial magnetic stimulation (TMS) with random variable pulse intervals determined by individual EEG characteristics for a time sufficient to modulate said brain activity wherein an improvement in a physiological condition or a clinical condition is achieved. In one embodiment, the variable pulse intervals are determined by subjecting the mammal to an EEG to create an EEG data set and analyzing the EEG data set to filter out "noise" which are unwanted frequencies higher and lower than the targeted EEG regions. A wavelet transform algorithm is a preferred method of filtering out noise signals or extracting information from the unknown portions from the EEG data. In general, sets of wavelets are needed to analyse complex data fully. The wavelet transform algorithm identifies a unique EEG signal pattern or profile for the mammal/patient. The EEG signal pattern is then used to generate a sequence of TTL (transistor-transistor logic) or other triggering pulses to program the TMS apparatus to provide variable pulse intervals and variable intensities. The pulses can be continuous or repetitive depending on the intensities of the pulses. At low intensities the pulses can be continuous. At higher intensities the pulses are preferably repetitive over time such as for example a 6 second pulse per minute. Other repetitive timing can also be used such as for example a 6 second pulse every 30 seconds, a 12 second pulse every 2 minutes and the like. Preferably, the magnetic stimulation is in a random fashion with idealized probability distribution such as Gaussian function, and characterized as period variability. Brain activity to be modulated can be any one or more desired frequency bandwidth(s) and includes the brain frequency bandwidth of 0-3 Hz, the brain frequency 3-8 Hz, the brain frequency bandwidth of 8-13 Hz, the brain frequency bandwidth of 13-20 Hz, and the brain frequency bandwidth of 20-50 Hz and any sub-bandwidth group within those ranges. If a frequency bandwidth between 8-13 Hz is targeted to treat a patient, the actual bandwidth used to treat that patient can be narrowed within or broadened beyond that bandwidth range depending on the period variation of patient's EEG oscillation, such as, for example, 110 ms-105 ms, i.e. a frequency bandwidth between 9.1 Hz and 9.5 Hz, or 167 ms-71 ms, i.e. a bandwidth between 6 Hz and 14 Hz. Success in the modulation is achieved when the targeted frequency bandwidth has an increase or decrease in amplitude or power density in addition to improvement in symptoms associated with the clinical and physiological conditions being treated. A patient is initially treated with random pulsed intervals based on the patient's initial EEG. Subsequent treatments are modified according to subsequent EEG data if there has been a change.

Physiological conditions and medical conditions that can be improved by modulating the brain activity according to the present invention are any conditions where abnormal brain activity contributes to a specific condition. Improvements are seen when the amplitude of the desired or targeted brain wave bands acquire an increase in amplitude or relative power density. Conditions that are treated include but are not limited to autism spectrum disorder (ASD), Alzheimer's Disease (AD), Post Traumatic Stress Disorder (PTSD), Traumatic Brain Injury (TBI), memory impairment, depression, pain, addiction substance abuse disorder (SUD), Obsessive Compulsive disorders (OCD), anxiety, Parkinson's disease, hypertension, libido dysfunction, motor function abnormalities, small height in young children, stress, obesity, sleep disorders, eating disorders, concentration/focus abnormalities, speech abnormalities, intelligence deficits, cognition abnormalities, Attention Deficit Hyperactivity Disorders (ADHD), schizophrenia, coma, bipolar disorders, tinnitus, fibromyalgia, chronic Lyme disease, Rheumatoid Arthritis (RA), other autoimmune diseases, gout, diabetes, arthritis, trauma rehab, athletic performance, cognitive improvement, and stroke.

Of particular interest in practicing the present invention, a patient is subjected to repetitive transcranial magnetic stimulation (rTMS) with random variable pulse intervals for a time sufficient to modulate a brain activity in the patient where an improvement in a physiological condition or a clinical condition is achieved. The patient is subjected to an EEG to create an EEG data set. The EEG data set is analyzed with a wavelet transform. The extracted signal by wavelet transform analysis is then used to program the random variable pulse intervals into the rTMS apparatus. The wavelet transform algorithm extracts a unique EEG signal and variable pulse interval pattern or profile that is administered in a randomized fashion and results in the desired improvements in the physiological or medical condition that is being treated.

The present invention relating to TMS is equally applicable to the electric stimulation of the brain, such as for example, by deep brain stimulation or transdermal stimulation with electricity such as, for example, the Alpha-Stim cranial electrotherapy stimulation (CES) device. The brain activity of a mammal is modulated by subjecting the mammal to electric stimulation with variable electric pulse intervals determined by individual EEG characteristics for a time sufficient to modulate said brain activity wherein an improvement in a physiological condition or a clinical condition is achieved. Preferably, the electric stimulation is in a random fashion with idealized probability distribution such as Gaussian function, and characterized as period variability.

DETAILED DESCRIPTION OF THE INVENTION

Figure 1:
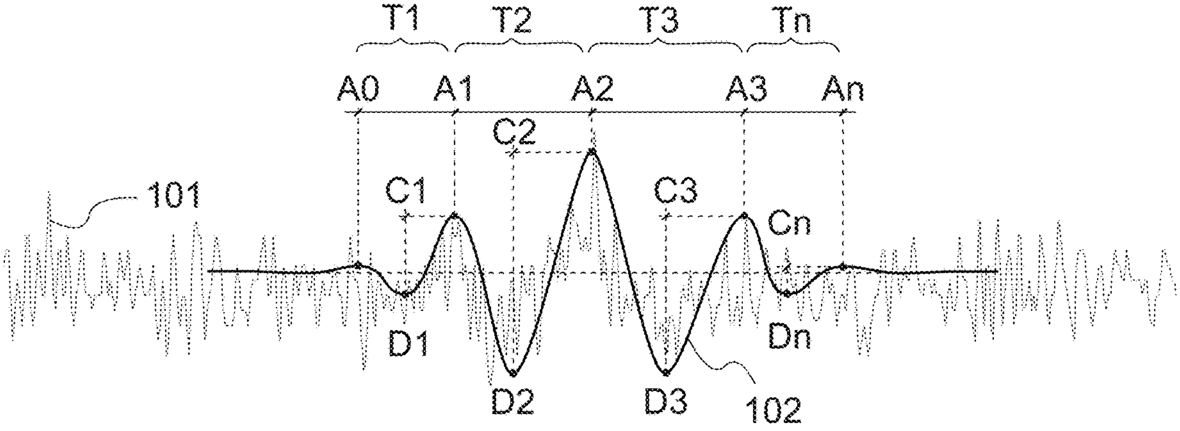
FIG. 1 shows EEG raw data and extracted signal by a wavelet analysis.

For the purposes of the present invention the following definitions are disclosed below:

The term "mammal" when used herein includes any mammal but especially humans. Non-human mammals include non-human primates, zoo animals, companion animals (dogs, cats) and performance animals such as race horses and breeding animals. Any reference to "humans" described herein will have applicability to other mammals that exhibit the same physiological or medical conditions. Any reference to "patient" when used herein has applicability to any mammal (preferably humans) that may experience the particular condition to which the patient reference is made. The term "variable pulsed interval" when referring to rTMS means that the magnetic stimulation is delivered over time at different time intervals instead of equal time intervals, i.e., frequency. "Stochastic resonance" means that a weak or undetected EEG signal of a patient can be amplified by administering to the patient magnetic stimulation that is variable and random similar to white noise being used to amplify weak or undetectable frequencies. The term "z-score" is a measure of how far or near a brain pattern is from the norm. The term "alpha spindles" refers to short burst of high frequency alpha band activity.

In practicing the present invention, an EEG is conducted on a patient experiencing physiological conditions and/or medical conditions in need of treatment. The raw EEG data is analyzed with a filtering algorithm to attenuate frequencies outside the EEG boundary that is being examined such as a wavelet transform algorithm resulting in a unique patient EEG wavelet signal. The pattern of the unique EEG signal is used to program the TTL pulses, or other triggers, generated by a TMS apparatus into random variable pulse intervals. Preferably, the TMS is delivered as a repetitive TMS (rTMS). rTMS is administered to the patient with variable pulse intervals for a time sufficient to modulate a brain activity which results in an improvement in the physiological condition or the clinical condition being treated.

In a preferred embodiment, random variable pulse intervals are employed in an rTMS protocol used for a time sufficient to modulate a brain activity resulting in an improvement in a physiological condition or a clinical condition. Preferably, the treatments are administered daily or 5 days/week for a month after which the patient's progress will be re-evaluated. As mentioned above the exact timing of the repetitive pulses is not critical. Thirty, six (6) second pulse every minute is preferred resulting in a 30-minute treatment period. The random variable pulse interval settings are achieved by programming the rTMS apparatus with the patient's EEG signal extracted by wavelet analysis to provide magnetic stimulation with random variable pulse intervals. The specific brain activity, or brain wave frequency bandwidth, to be modulated is dictated by the patient's EEG. A preferred brain frequency bandwidth is 8-13 Hz. The maximum intensity setting of the magnetic pulses is generally limited to the patient's motor threshold or lower but can be administered over the patient's motor threshold. It is preferred to set the peak pulse power/intensity of the rTMS to about 80% of the patient's motor threshold. Generally, the power/intensity is from 0.1-95% of motor threshold, 10-90% of motor threshold, 40-80% of motor threshold or 60-90% of the motor threshold.

The rTMS treatments according to the present invention are administered according to well-known protocols employing magnetic coils. The time of actual magnetic stimulation over a set period of time will vary based on each clinical presentation. It is preferred to administer the magnetic stimulation for six continuous seconds per minute of the rTMS session. Sessions can last from 15 to 60 minutes and preferably about 30 minutes. Magnetic coils are placed in close proximity or against a patient's head preferably adjacent to the area of the head where the desired brain frequency wavelengths predominate in the patient's brain. For example, if treating a patient with a frequency bandwidth in the 8-13 Hz range then the magnetic rTMS coils are generally placed against the frontal lobe area (forehead) of the patient where the random variable pulses are administered. For treating a patient with random variable pulses in more than one frequency bandwidth range, the magnetic coils are positioned adjacent to brain regions that the patient's EEG has identified as having poor coherence, low energy and/or regions that are non-synchronous.

Patients/mammals can be treated for any one or more of the brain wave frequency ranges described herein. When more than one brain wave frequency bandwidth range is targeted the rTMS random variable pulsed intervals can be administered simultaneously or sequentially in one treatment session. When treating multiple brain wave frequency bandwidth ranges, the rTMS can be delivered by an rTMS device that can deliver random variable pulsed intervals to more than one area of the patient's head. Alternatively, multiple rTMS devices can be used to deliver the desired random variable pulsed intervals to the desired areas.

A patient in need of treatment is subjected to an EEG resulting in an EEG data set. The EEG data is then analyzed with a wavelet transform algorithm resulting in the patient's EEG signal pattern 102 (FIG. 1). The patient's EEG signal extracted by wavelet analysis is then used to determine the variable pulse intervals used in the patient's rTMS treatment. In another embodiment the EEG data set is analyzed with a filtering algorithm such as a band-pass filter to attenuate extraneous frequencies above or below the EEG boundaries being examined. Other filtering algorithms include but are not limited to artifact rejecting analysis, autocorrelation analysis and zero-crossing analysis. Other algorithms can be used to determine the pulse parameters such as statistical analysis for the mean and standard deviation of a desired EEG frequency boundary.

Referring to FIG. 1, the EEG raw data profile 101 is analyzed with a wavelet transform algorithm resulting in the patient's individual wavelet pattern 102. The EEG signal pattern is then analyzed to determine a time sequence with period variation $A_0$, $A_1$, $A_2$ . . . $A_n$ and amplitude settings with intensity variation $C_1$-$D_1$, $C_2$-$D_2$, $C_3$-$D_3$ . . . $C_n$-$D_n$. The power settings are determined by the magnitude of each EEG wave measured between the peak (C) and the prior trough (D). The rTMS trigger pulse occurs at the peak of each wave determined by the wavelet analysis, and in FIG. 1, that would involve "n" number of pulses—one pulse at $A_1$, $A_2$, . . . $A_n$. It should be understood that n>1 and there could be more or less than 3 pulses per train of pulses depending on the EEG and wavelet data. The timing of the pulses is shown by the T values $T_1$, $T_2$, and $T_n$ which are determined by the period between EEG waves depicted by the wavelet transform analysis. When targeting brain waves in the 8-13 Hz range the timing of the pulses will vary but will be between 75-125 milliseconds (ms).

Figure 2:
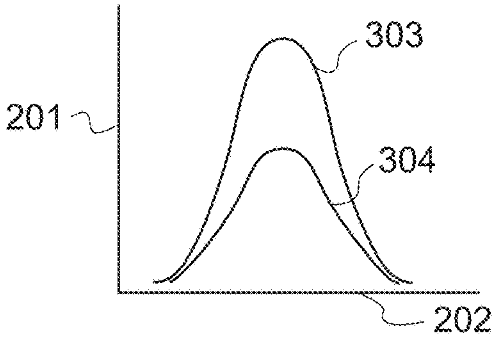
FIG. 2 shows the results of a patient's EEG power spectra before and after treatment.
Figure 3:
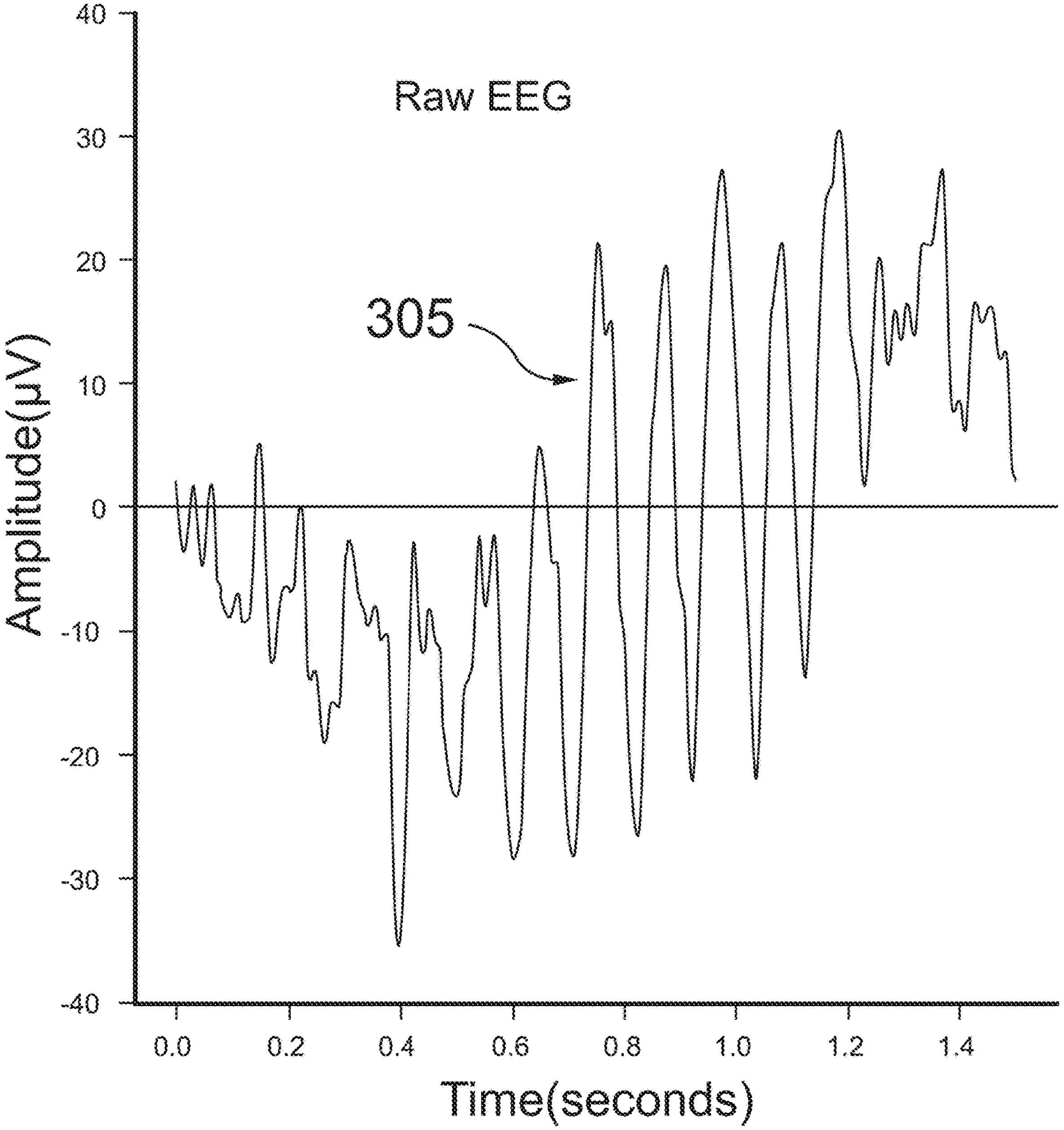
FIG. 3 represents raw EEG.
Figure 4:
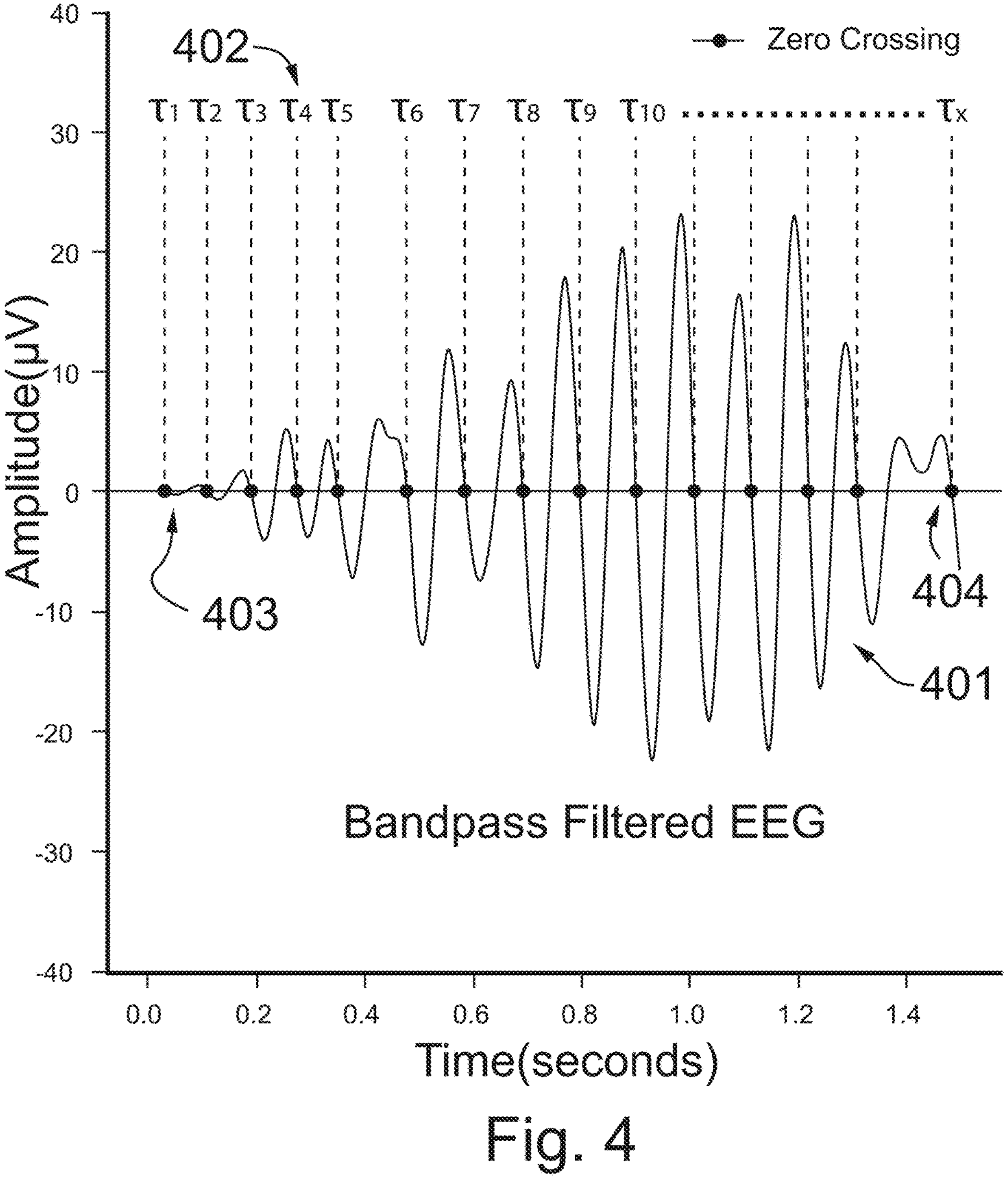
FIG. 4 represents an extracted signal from EEG data by analyzing the EEG data with a bandpass filter.

FIG. 2 is a graph of power spectra of a patient's EEG and plots power 201 against frequency 202 showing pre-treatment 304 and a post-treatment 303 profiles.

Once a patient's EEG signal is identified by wavelet transform analysis it is used to program the rTMS apparatus to deliver the variable pulse interval settings to be used in that patient's rTMS treatment.

Figure 5:
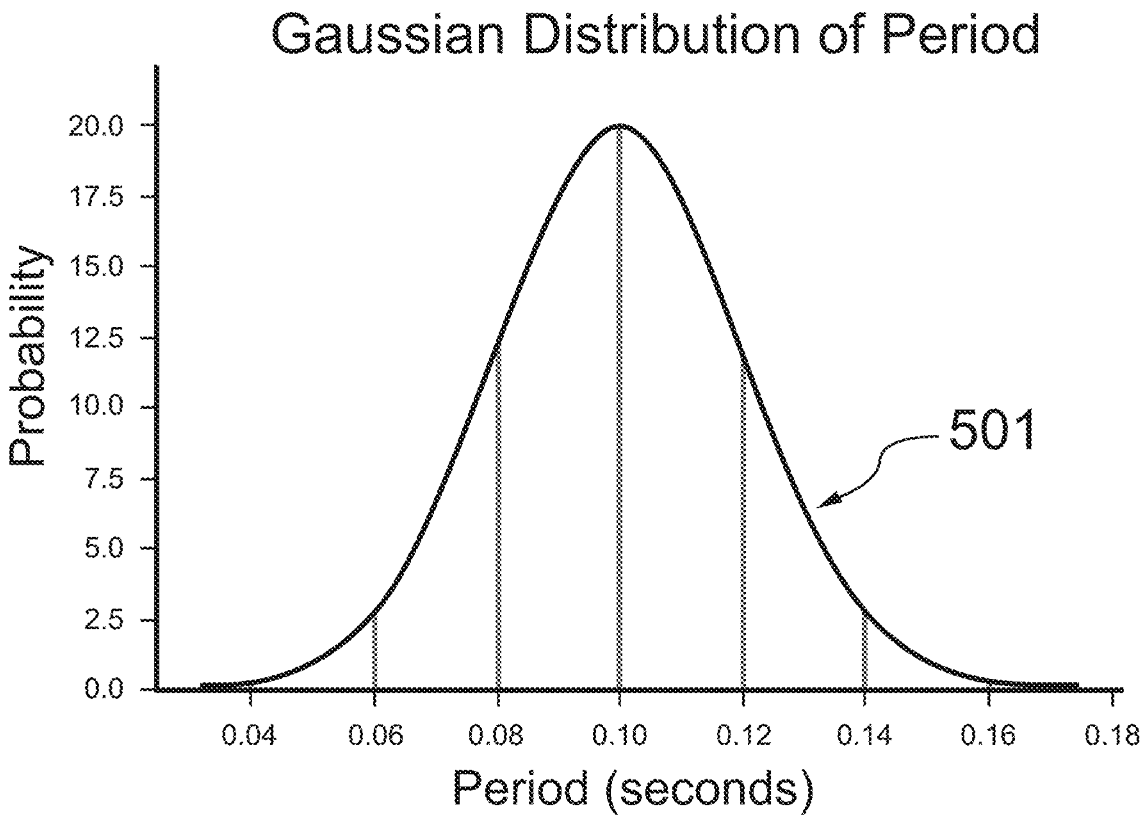
FIG. 5 is a Gaussian distribution of the extracted signal of FIG. 4.
Figure 6:
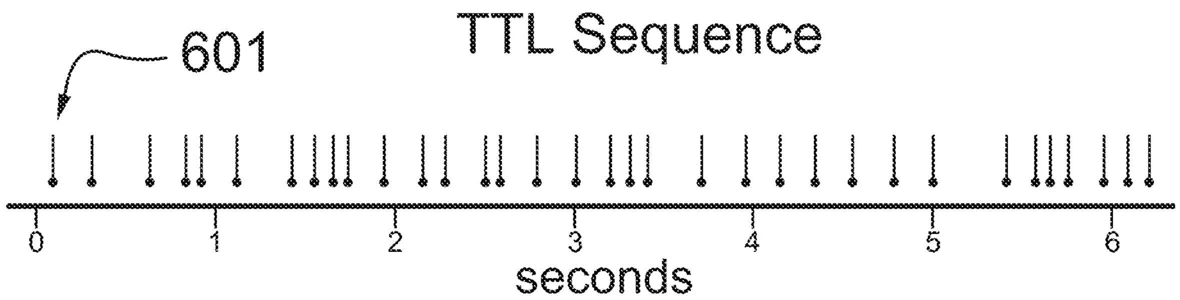
FIG. 6 shows a TTL (transistor-transistor logic) sequence used to determine the random pulses used to treat a patient.

In a further embodiment of the present invention, a patient in need of treatment is administered an EEG resulting in an EEG data set. The EEG data set is then analyzed with an algorithm to attenuate extraneous frequencies above or below the EEG boundaries being examined resulting in the patient's EEG variability profile. The magnetic stimulation is achieved with idealized random pulse intervals within the detected or targeted EEG frequency boundary such as the 8-13 Hz range. The EEG record is analyzed in the time domain to identify the variability profile by mean period and standard deviation of the dominant components of interest. The data is then idealized to form a Gaussian distribution (FIG. 5) to generate the desired number of randomized transistor-transistor logic (TTL) pulse trains to treat the patient. Usually, a 6-second pulse train delivered every minute is employed. Treatments typically last 30 minutes delivering 30, 6-second pulse trains (6 seconds stimulation followed by 54 seconds of rest). The patient's EEG variability profile is used to determine the random variable pulse intervals used in the patient's rTMS treatment and is preferably characterized as period variability. In another embodiment the EEG data set is analyzed with a band-pass filter to attenuate extraneous frequencies above or below the EEG boundaries being examined. In additional embodiments artifact rejecting analysis, autocorrelation analysis, zero-crossing analysis and statistical analysis for the mean and standard deviation of a desired EEG frequency boundary are employed to determine the random pulse intervals used in the patient's treatment.

In another embodiment, a stochastic resonance stimulus protocol (SRSP) is used to modulate EEG brain activity in a patient in need thereof. The SRSP shows a more EEG tuning effect over prior art single frequency protocols. The SRSP employs the patient's EEG variability profile and stimulates the patient with idealized random pulse intervals within the detected EEG frequency boundary. For treatment in the alpha region (8-13 Hz) the SRSP analyses the EEG record in the time domain to identify the variability profile by mean period and standard deviation of dominant components of interest. The resulting data is then idealized to a Gaussian distribution to generate randomized transistor-to-transistor logic (TTL) pulse trains to be delivered to the patient via the rTMS apparatus. Typically, 30 pulse trains are delivered to a patient every 54 seconds resulting in a treat that last 30 minutes. The number of standard deviations selected in generating a specific patient protocol depends on the z-scores of the patient compared to a normative database. The treatment parameters that can be used in devising a patient's specific treatment protocol include one or more of EEG period distribution, power spectral profile, AB ratio (amplitude/bandwidth) in the dominant frequency band, coherence and regional channel entropy, normalization of a Gaussian distribution calculated with a Box-Muller transform or a white noise pattern, ie. pink or blue.

Referring to FIGS. 3-6, the EEG raw data (FIG. 3) profile 301 is analyzed with an algorithm to reduce noise resulting in the patient's EEG variability pattern or profile (FIG. 4) referred to as the Band-Pass Filtered EEG or EEG variability profile. The EEG variability profile is then analyzed to determine a time sequence with period variation tau ($\tau$) $\tau_0$, $\tau_1$, $\tau_2$ . . . $\tau_X$ which are labeled as zero crossing (•). Zero crossings are identified every other time the signal crosses through the zero (0) amplitude line. The entire EEG record is analyzed in the time domain to identify the variability profile by mean period and standard deviation of components of interest. Data from the EEG variability profile (pattern) is then idealized to a Gaussian distribution (FIG. 5) to generate thirty (30) 6 second randomized TTL pulse trains (FIG. 6) to treat the patient over a 30-minute period. The number of standard deviations selected in generating a patient's treatment protocol will vary depending on the z-scores of the patient compared to a normative database. The treatment parameters that can be used in devising a patient's specific treatment protocol include one or more of EEG period distribution, power spectral profile, AB ratio (amplitude/bandwidth) in the dominant frequency band, coherence, regional channel entropy, normalization of a Gaussian distribution calculated with a Box-Muller transform or a white noise pattern, ie. pink or blue.

When targeting brain waves in the 8-13 Hz range the timing of the pulses will vary within or beyond the range between 75 and 125 milliseconds (ms). Data in treating patients with TMS using random variable pulse intervals has shown a more EEG tuning effect over the individual's prior TMS treatments using a single intrinsic frequency.

In another embodiment of the present invention where electric stimulation is desired, a patient in need of treatment is administered an EEG resulting in an EEG data set. The EEG data set is then analyzed with an algorithm to attenuate extraneous frequencies above or below the EEG boundaries being examined resulting in the patient's EEG variability profile. The electric stimulation is achieved with idealized random electric pulse intervals within the detected or targeted EEG frequency boundary such as the 8-13 Hz range. The EEG record is analyzed in the time domain to identify the variability profile by mean period and standard deviation of the dominant components of interest. The data is then idealized to form a Gaussian distribution to generate the desired number of randomized electric pulses to treat the patient. Usually, a 6-second electric pulse delivered every minute is employed. Treatments typically last 30 minutes delivering 30, 6-second electric pulse (6 seconds stimulation followed by 54 seconds of rest). The patient's EEG variability profile is used to determine the random electric pulse intervals used in the patient's electric stimulation treatment and is preferably characterized as period variability. In another embodiment the EEG data set is analyzed with a band-pass filter to attenuate extraneous frequencies above or below the EEG boundaries being examined. In additional embodiments artifact rejecting analysis, autocorrelation analysis, zero-crossing analysis and statistical analysis for the mean and standard deviation of a desired EEG frequency boundary are employed to determine the random electric pulse intervals used in the patient's treatment.

The following examples illustrate the practice of the present invention but should not be construed as limiting its scope.

Example 1

Figure 7:
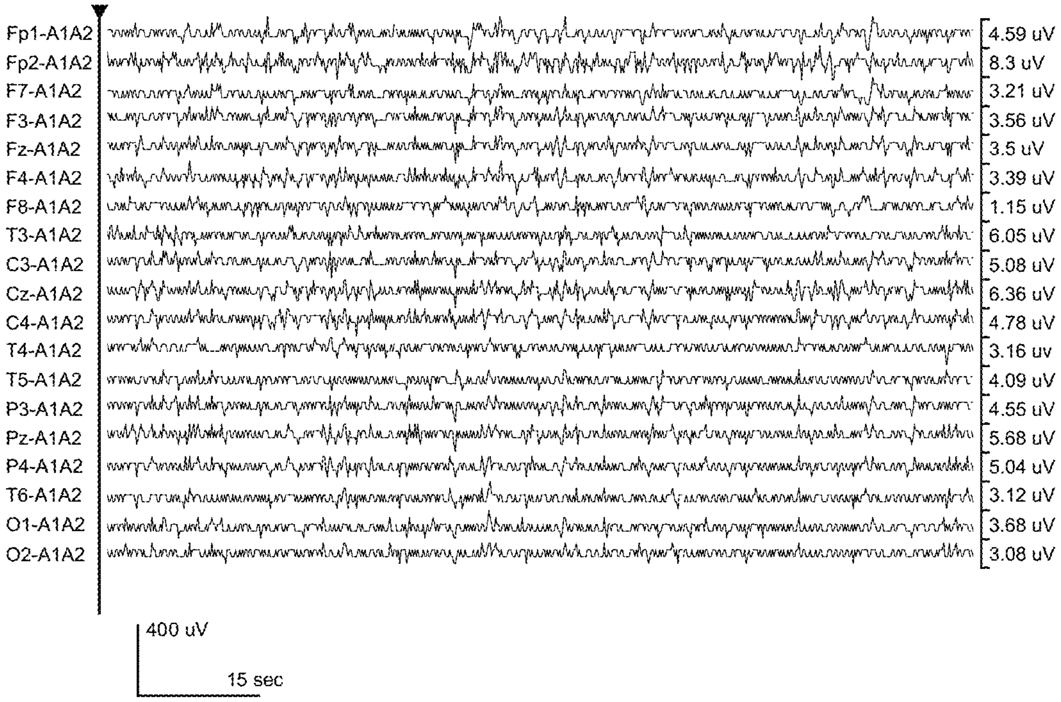
FIG. 7 shows the pre-treatment EEG data, the power spectra and a topography of the brain activity of the patient in Example 1.
Figure 7:
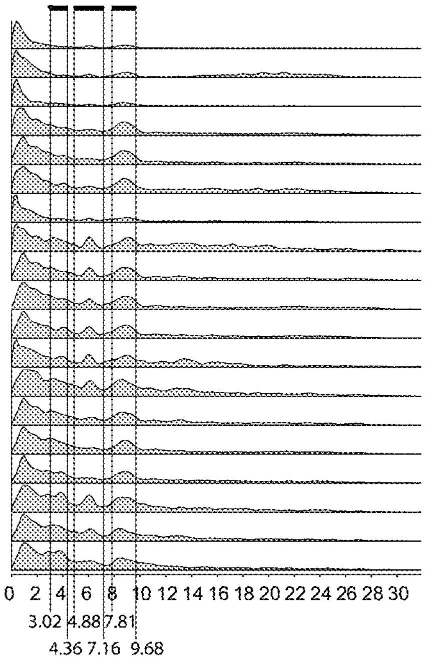
Figure 7:
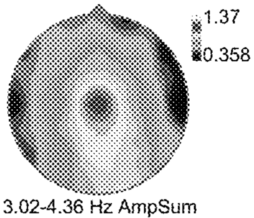
Figure 7:
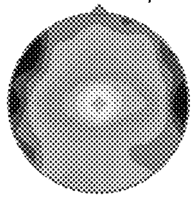
Figure 7:
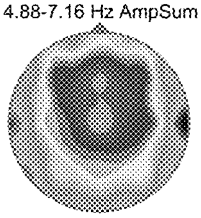
Figure 7A:
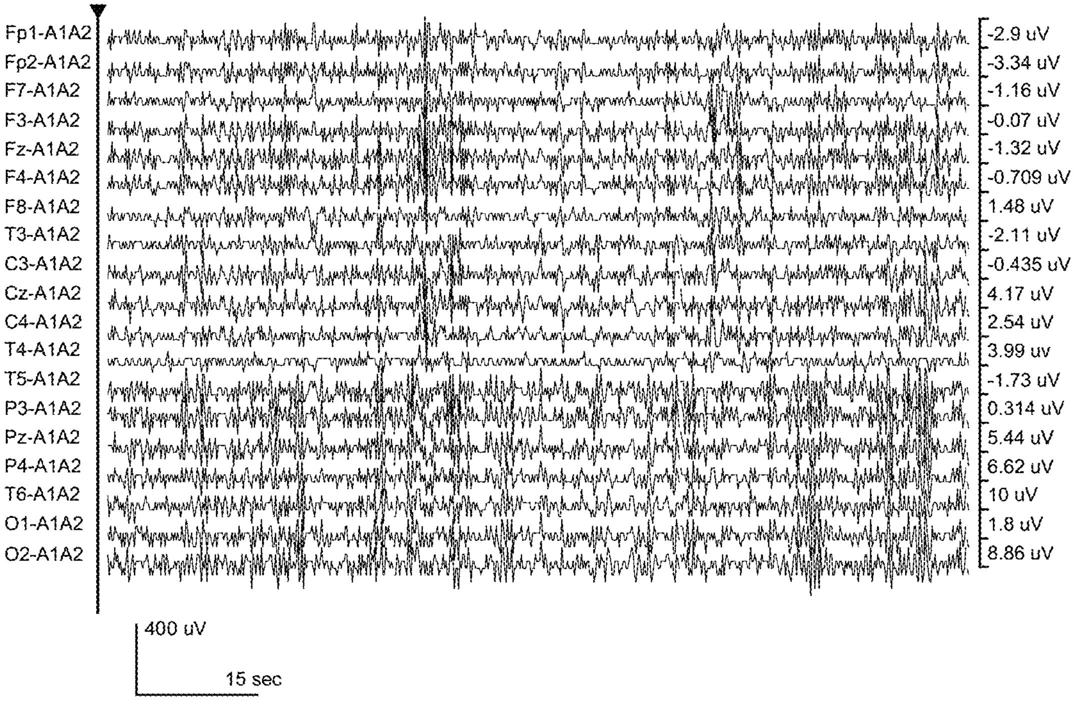
FIG. 7A shows the post-treatment EEG data, the power spectra and a topography of the brain activity of the patient in Example 1.
Figure 7A:
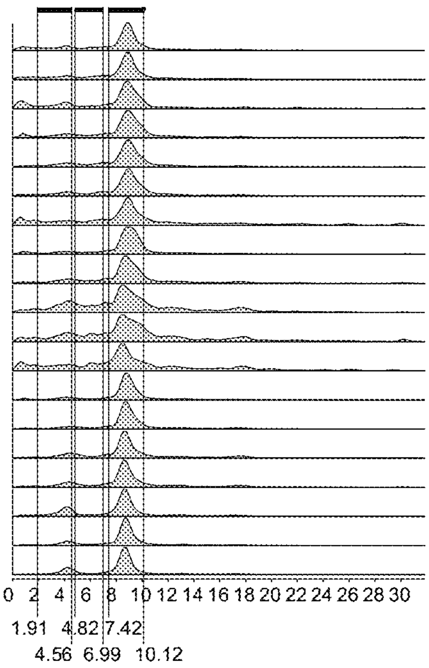
Figure 7A:
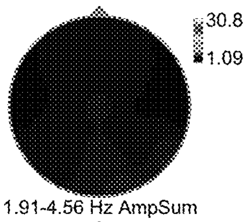
Figure 7A:
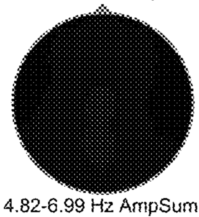
Figure 7A:
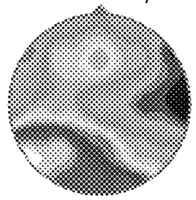

A 69-year-old male patient with chronic Attention Deficit Disorder (ADD) and anxiety was treated with random variable repetitive transcranial magnetic stimulation (rTMS) according to the present invention. A pre-treatment EEG of the patient (FIG. 7) shows excessive slow waves globally in delta and theta frequency bands, while dominant activity remains in alpha frequency. Wavelet analyses coupled with bandpass filtering and zero-crossing count of the entire 10 min data epoch were performed to yield an EEG period variability profile by mean period and standard deviation of the dominant components of interest. The data was then idealized to a Gaussian distribution to generate 30, 6-second randomized TTL pulse trains with a mean pulse period of 107.5 ms varied between 108.7 ms and 103.1 ms to treat the patient for a 30-minute, one 6-second pulse train per minute treatment. The patient's post-treatment EEG (FIG. 7A) shows significant improvement in alpha frequency selectivity and synchronization and reduction in slow wave components as compared to baseline. The patient reported to have improvement in night time sleep, mood, and attention span following 4 days of this daily treatment.

Example 2

Figure 8:
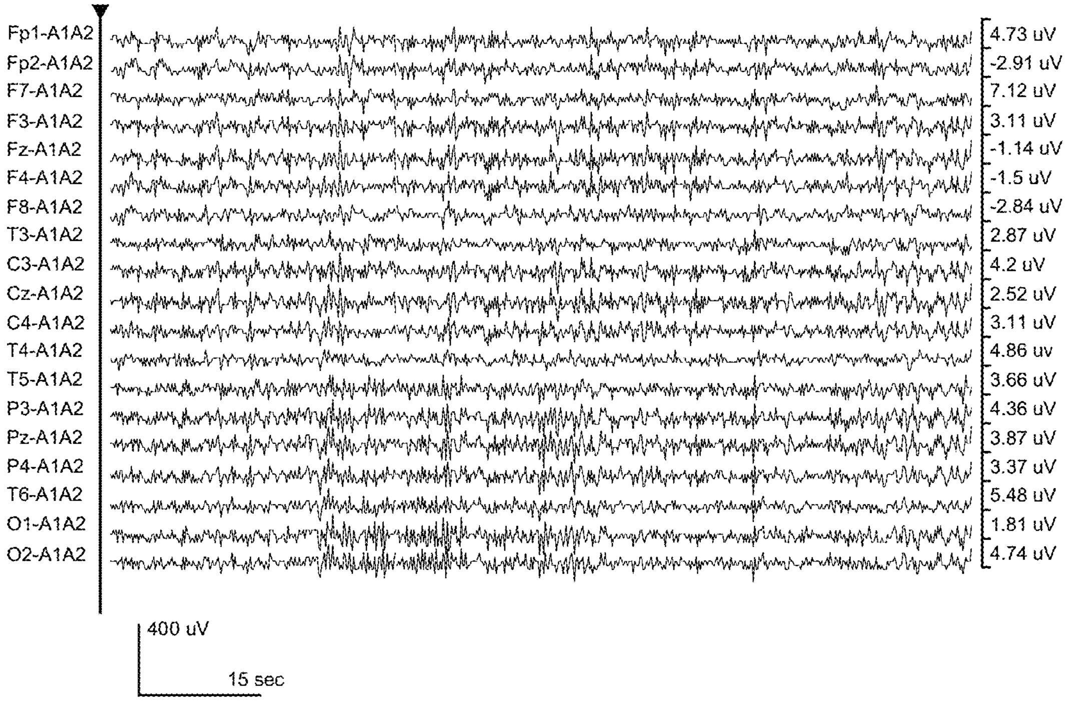
FIG. 8 shows the pre-treatment EEG data, the power spectra and a topography of the brain activity of the patient in Example 2.
Figure 8:
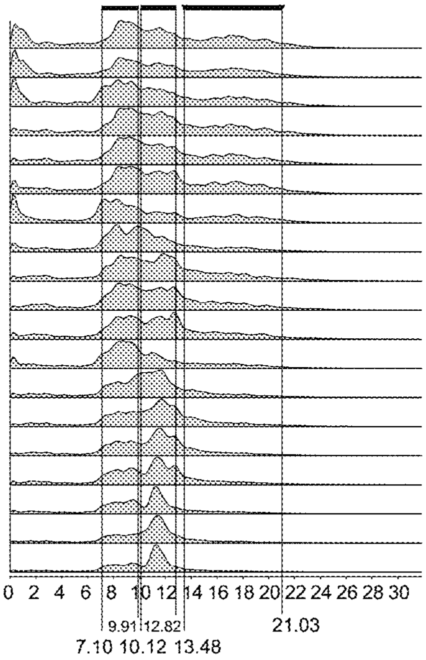
Figure 8:
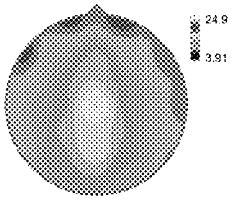
Figure 8:
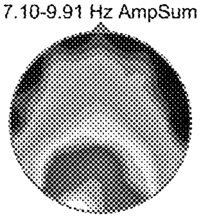
Figure 8:
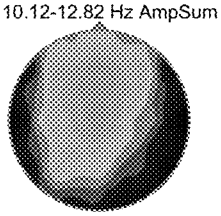
Figure 8A:
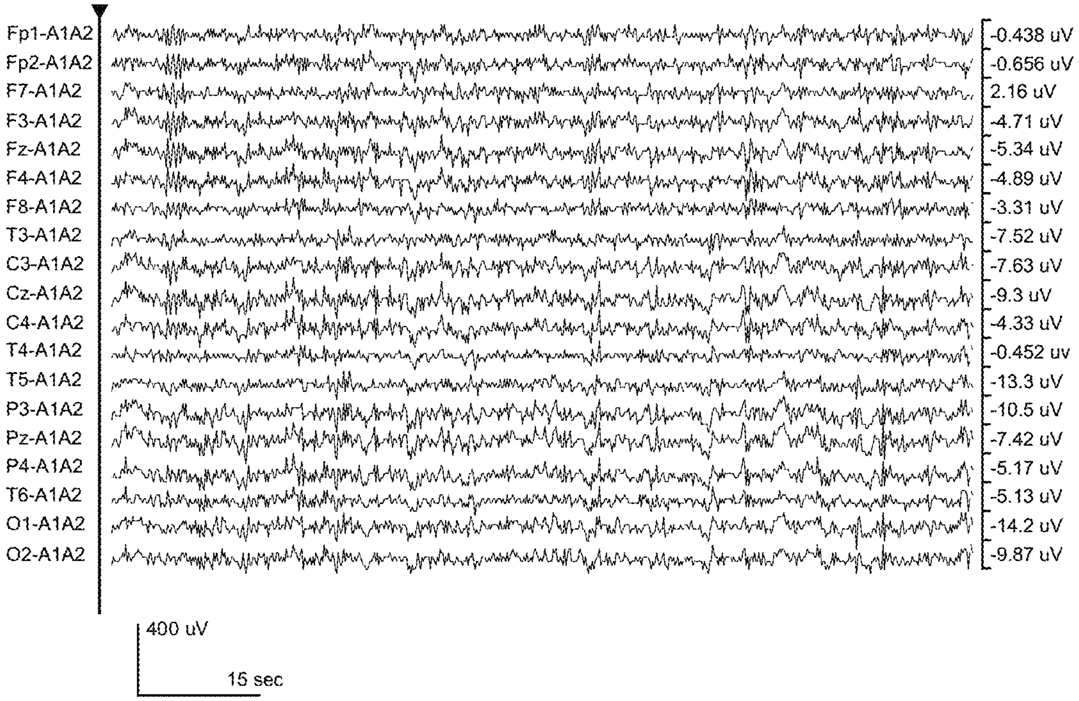
FIG. 8A shows the post-treatment EEG data, the power spectra and a topography of the brain activity of the patient in Example 2.
Figure 8A:
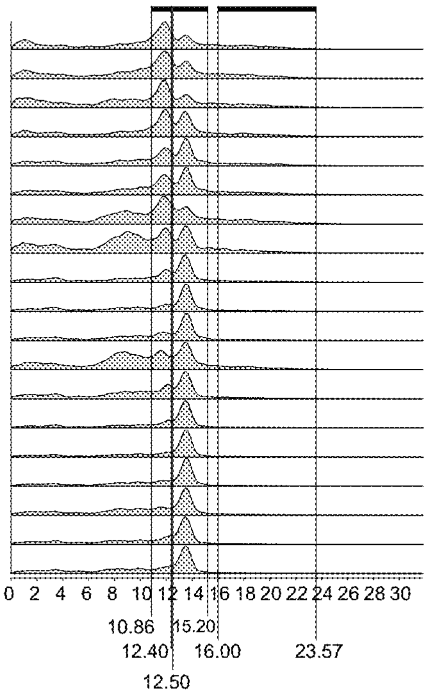
Figure 8A:
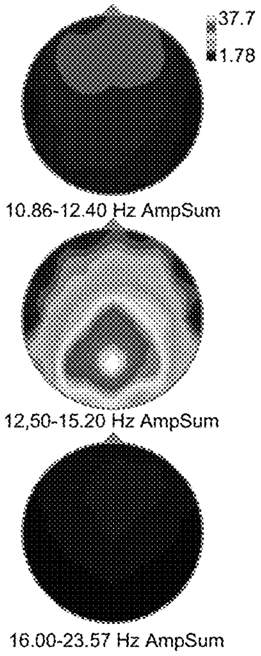

A 59-year old male patient with severe anxiety for 20 plus years was treated with random variable repetitive transcranial magnetic stimulation (rTMS) according to the present invention. A pre-treatment EEG of the patient (FIG. 8) shows increased beta activity and highly desynchronized alpha activities with low frequency selectivity, primarily in the frontal and central areas. The pre-treatment EEG was analyzed with wavelet analyses coupled with bandpass filtering and zero-crossing count of the entire 7 min data epoch to yield an EEG period variability profile by mean period (94.3 ms) and standard deviation (158.7 ms) of the dominant components of interest. The data was then idealized to a Gaussian distribution to generate 30, 6-second randomized TTL pulse trains to treat the patient for a 30-minute, one 6-second pulse train per minute treatment. The patient's post treatment EEG (FIG. 8A) after 4 days of treatments shows great improvement in alpha frequency selectivity and synchronization, and reduction in spontaneous beta activities. The patient reported to have significant reduction in anxiety.

Example 3

Figure 9:
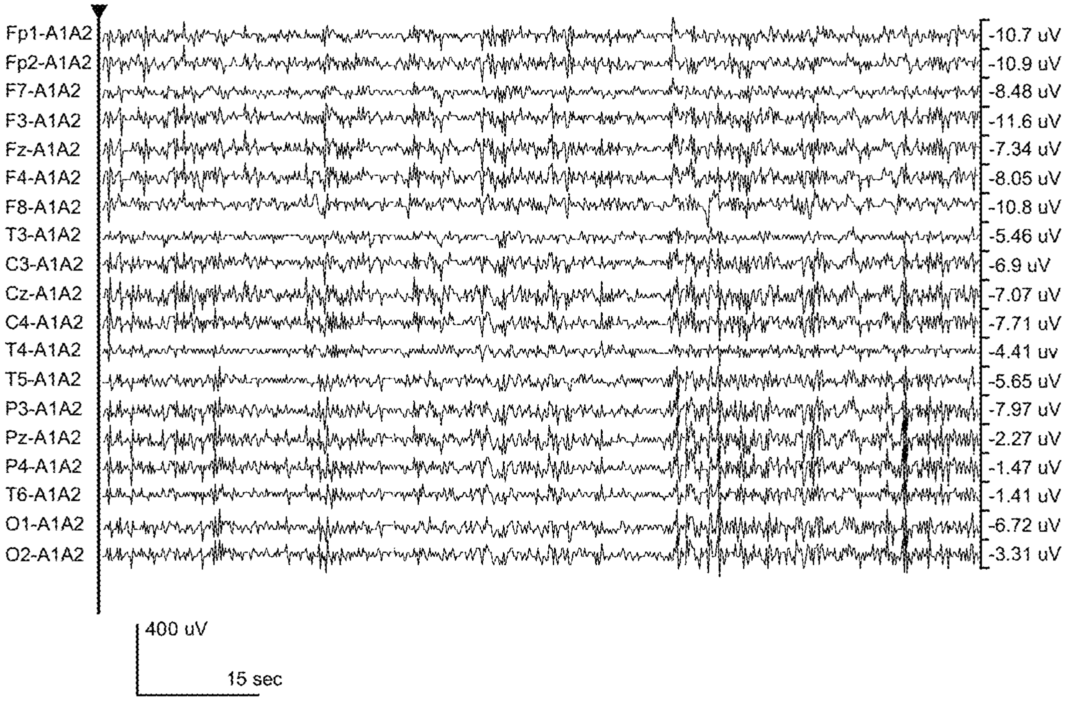
FIG. 9 shows the pre-treatment EEG data, the power spectra and a topography of the brain activity of the patient in Example 3.
Figure 9:
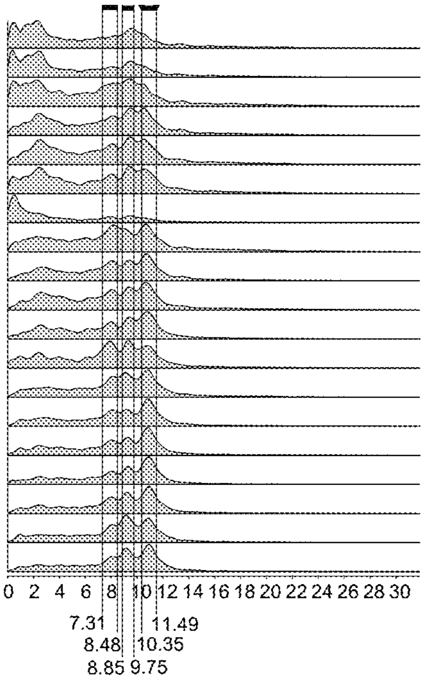
Figure 9:
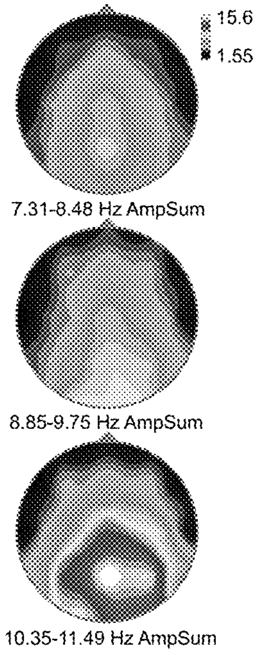
Figure 9A:
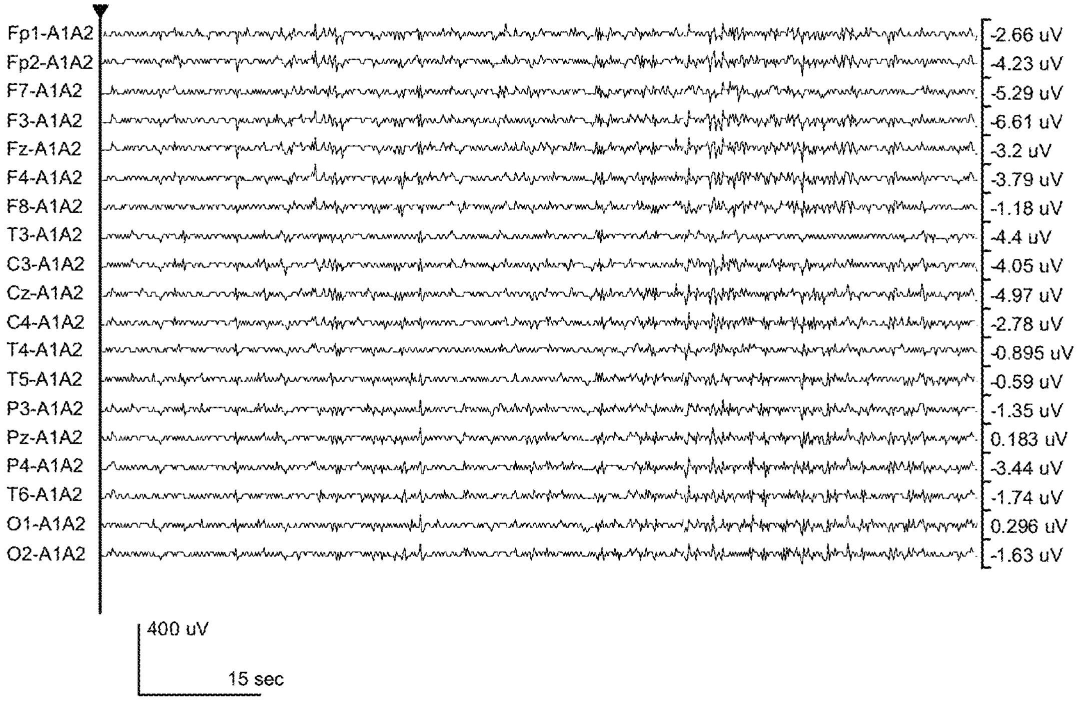
FIG. 9A shows the post-treatment EEG data, the power spectra and a topography of the brain activity of the patient in Example 3.
Figure 9A:
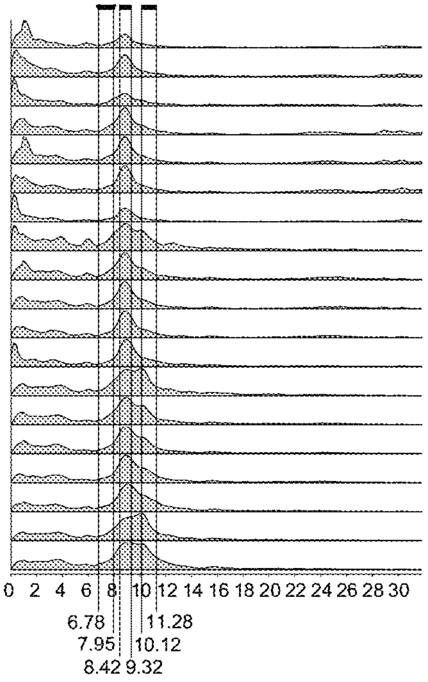
Figure 9A:
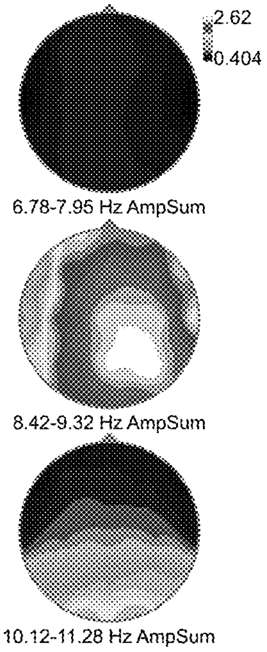

An 84-year-old female patient who has experienced difficulties in memory and night time sleep was treated with random variable repetitive transcranial magnetic stimulation (rTMS) according to the present invention. A pre-treatment EEG of the patient (FIG. 9) shows multiple distinct frequency components adjacent to the dominant alpha rhythm. Wavelet analyses coupled with bandpass filtering and zero-crossing count of the entire 7 min data epoch were performed to yield an EEG period variability profile by mean period (9.4 ms) and standard deviation (117.6 ms) of the dominant components of interest. The data was then idealized to a Gaussian distribution to generate 30, 6-second randomized TTL pulse trains with a mean pulse period of 116.3 ms varied between 119.1 ms and 112.4 ms to treat the patient for a 30-minute, one 6-second pulse train per minute. The patient's post-treatment EEG (FIG. 9A) shows significant improvement in alpha frequency selectivity and synchronization along with the alpha mean frequency down shift from 9.4 Hz to 8.5 Hz. It also shows reduction in slow waves in delta and theta frequency bands. The patient reported to have improvement in mood, sleep, and memory following 4 days of this daily treatment.

Example 4: Confirmation of Stochastic Resonance

Figure 10:
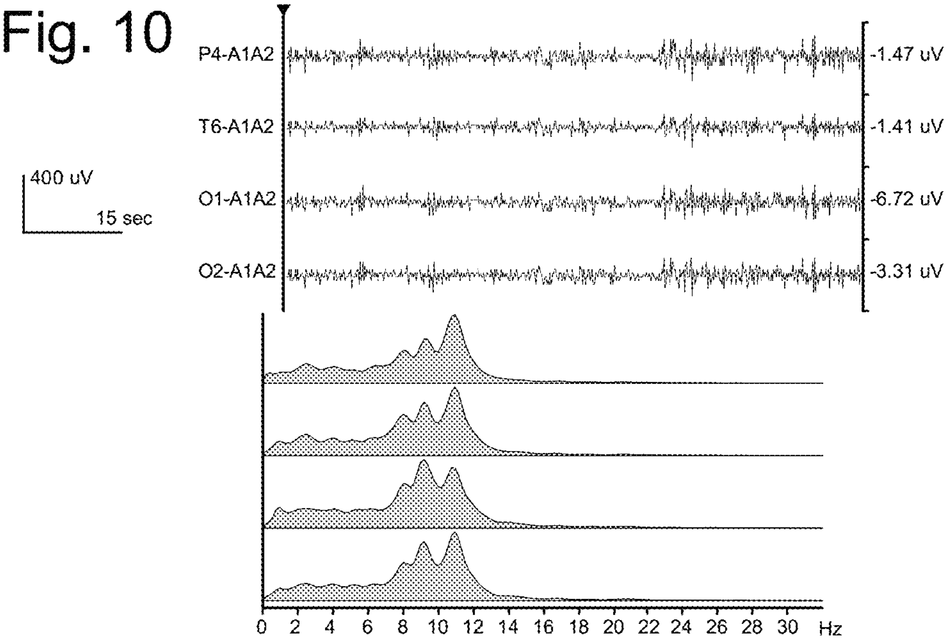
FIG. 10 shows the power spectral analysis of the pre-treatment EEG of the patient in Example 3.
Figure 10A:
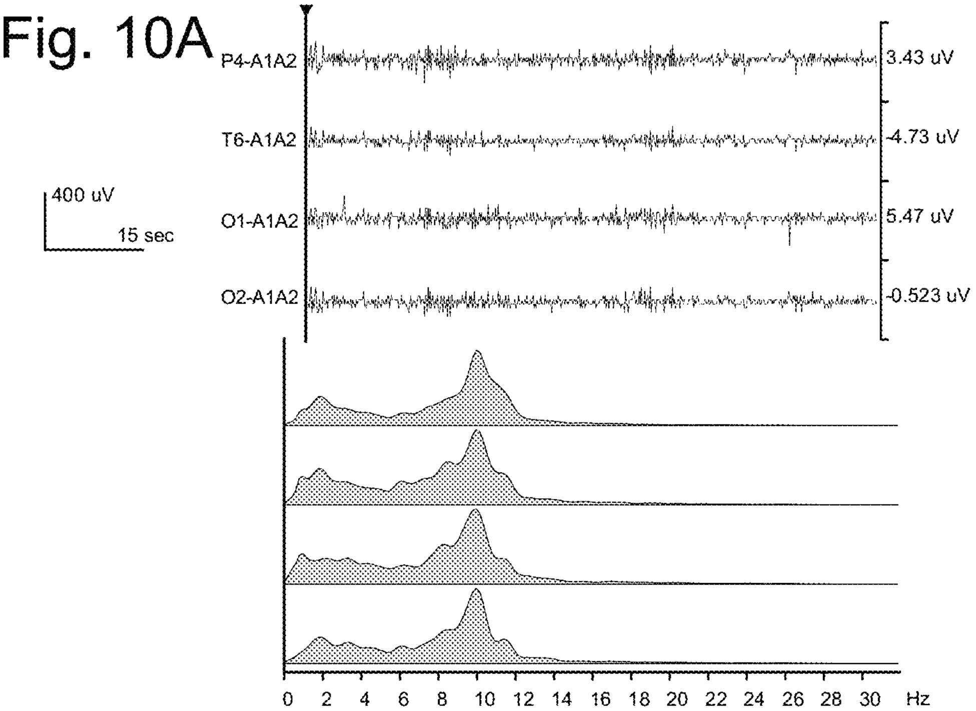
FIG. 10A shows the power spectral analysis of the post-treatment EEG of the patient in Example 3.

A Zoom-in power spectral analysis of pre-treatment EEG (FIG. 10) and post-treatment EEG (FIG. 10A) in the posterior channels of patient in Example 3 are compared. The post-treatment alpha EEG (FIG. 10A) had significant increase in frequency selectivity while other lower frequency components were reduced. This confirms that a stochastic resonant response was achieved.

Additionally, the present invention relates to an improved rTMS apparatus wherein the improvement comprises a means for delivering rTMS pulses as variable pulse intervals. In one embodiment, the rTMS apparatus is programmed to deliver random variable pulse intervals. Preferably the peak power or intensity delivered to a patient is below the patient's motor threshold and preferably at 40-90% of the patient's motor threshold while the rest of the pulse intensity varies proportional to the corresponding EEG signal wave amplitude.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A method of treating a patient's brain which comprises:

a) subjecting the patient to an EEG to create an EEG data set, b) analyzing the EEG data set to identify alpha spindle events resulting in an EEG signal pattern, c) using the EEG signal pattern to program a TMS apparatus to deliver magnetic stimulation (TMS) having random pulse intervals and d) subjecting the patient to random transcranial magnetic stimulation from said programmed TMS apparatus.

2. The method of claim 1 wherein the alpha spindles are identified by analysis of the EEG data set with a discounted autoregressive modeling (DAR).

* * * * *